(12) United States Patent
Leisinger et al.

(10) Patent No.: US 8,533,921 B2
(45) Date of Patent: Sep. 17, 2013

(54) SPIRAL ASSEMBLY TOOL

(75) Inventors: Steven R. Leisinger, Columbia City, IN (US); Daniel N. Huff, Warsaw, IN (US); Donald E. McNulty, Warsaw, IN (US); Rodney N. Satterthwaite, Huntington, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 162 days.

(21) Appl. No.: 12/815,915

(22) Filed: Jun. 15, 2010

(65) Prior Publication Data

US 2011/0302760 A1   Dec. 15, 2011

(51) Int. Cl.
*B23P 19/04* (2006.01)
*A61B 17/58* (2006.01)

(52) U.S. Cl.
USPC .................... 29/244; 606/99; 29/264; 29/252

(58) Field of Classification Search
USPC .................. 74/56, 53; 29/281.5, 264, 283.5, 29/252; 606/99, 102; 623/909, 911; 81/471; 254/104; 269/66
See application file for complete search history.

(56) References Cited

U.S. PATENT DOCUMENTS

| | | | |
|---|---|---|---|
| 3,810,312 A | 5/1974 | Carson | |
| 3,889,558 A | 6/1975 | Duncan | |
| 4,305,394 A | 12/1981 | Bertuch | |
| 4,601,289 A | 7/1986 | Chiarizzio et al. | |
| 4,959,066 A | 9/1990 | Dunn et al. | |
| 5,002,578 A | 3/1991 | Luman | |
| 5,002,581 A | 3/1991 | Paxson et al. | |
| 5,057,112 A | 10/1991 | Sherman et al. | |
| 5,190,550 A | 3/1993 | Miller et al. | |
| 5,342,363 A | 8/1994 | Richelsoph | |
| 5,352,231 A | 10/1994 | Brumfield et al. | |
| 5,409,492 A | 4/1995 | Jones et al. | |
| 5,540,687 A | 7/1996 | Fairley et al. | |
| 5,653,765 A | 8/1997 | McTighe et al. | |
| 5,858,020 A | 1/1999 | Johnson et al. | |

(Continued)

FOREIGN PATENT DOCUMENTS

DE  20114835 U1   1/2002
EP  1000595 A1   5/2000

(Continued)

OTHER PUBLICATIONS

European Search Report for Corresponding Patent Application No. EPO11169798.3-2310 Dated Aug. 10, 2011, 7 Pages.

(Continued)

*Primary Examiner* — Lee D Wilson
*Assistant Examiner* — Jamal Daniel

(57) ABSTRACT

An assembly tool for assembly of a first component of a prosthesis to a second component of the prosthesis for use in joint arthroplasty. The tool includes a first member operably associated with the first component and defines a first member longitudinal axis thereof. A second member is operably associated with the second component and defines a second member longitudinal axis thereof. A washer system is coupled to the second member. A drive mechanism is coupled to washer system, such that as the drive mechanism is activated, the washer system rotates about the second member longitudinal axis and expands along the second member longitudinal axis, wherein such movement further causes the second member to move relative to the first member along the second member longitudinal axis.

12 Claims, 8 Drawing Sheets

(56) References Cited

U.S. PATENT DOCUMENTS

| | | | |
|---|---|---|---|
| 5,876,459 A | 3/1999 | Powell | |
| 5,938,701 A | 8/1999 | Hiernard et al. | |
| 6,080,162 A | 6/2000 | Dye et al. | |
| 6,110,179 A | 8/2000 | Flivik et al. | |
| 6,165,177 A | 12/2000 | Wilson et al. | |
| 6,193,759 B1 | 2/2001 | Ro et al. | |
| 6,238,435 B1 | 5/2001 | Meulink et al. | |
| 6,330,845 B1 | 12/2001 | Meulink | |
| 6,361,563 B2 | 3/2002 | Terrill-Grisoni et al. | |
| 6,491,696 B1 | 12/2002 | Kunkel | |
| 6,706,072 B2 | 3/2004 | Dwyer et al. | |
| 6,743,235 B2 | 6/2004 | Subba Rao | |
| 6,883,217 B2 | 4/2005 | Barrette et al. | |
| 6,905,515 B1 | 6/2005 | Gilbertson | |
| 7,022,141 B2 | 4/2006 | Dwyer et al. | |
| 7,066,042 B2 * | 6/2006 | Andrews et al. | 74/110 |
| 7,188,556 B1 * | 3/2007 | Rinner | 81/467 |
| 7,297,166 B2 | 11/2007 | Dwyer et al. | |
| 7,363,838 B2 * | 4/2008 | Abdelgany | 81/60 |
| 7,582,092 B2 | 9/2009 | Jones et al. | |
| 7,585,329 B2 | 9/2009 | McCleary et al. | |
| 2003/0149487 A1 | 8/2003 | Doubler | |
| 2004/0054373 A1 | 3/2004 | Serra et al. | |
| 2004/0073315 A1 | 4/2004 | Justin et al. | |
| 2004/0122437 A1 | 6/2004 | Dwyer et al. | |
| 2004/0122439 A1 | 6/2004 | Dwyer et al. | |
| 2004/0122440 A1 | 6/2004 | Daniels et al. | |
| 2004/0122525 A1 | 6/2004 | Daniels et al. | |
| 2004/0172139 A1 | 9/2004 | Dwyer et al. | |
| 2004/0267267 A1 | 12/2004 | Daniels et al. | |
| 2004/0267373 A1 | 12/2004 | Dwyer et al. | |
| 2005/0033444 A1 | 2/2005 | Jones et al. | |
| 2006/0027027 A1 | 2/2006 | Serra et al. | |
| 2006/0217737 A1 | 9/2006 | Iversen | |
| 2006/0260440 A1 | 11/2006 | Abdelgany | |
| 2007/0005144 A1 | 1/2007 | Leisinger et al. | |
| 2007/0123908 A1 | 5/2007 | Jones et al. | |
| 2008/0091212 A1 * | 4/2008 | Dwyer et al. | 606/99 |
| 2009/0112216 A1 | 4/2009 | Leisinger | |
| 2009/0112218 A1 | 4/2009 | McCleary et al. | |
| 2009/0187251 A1 | 7/2009 | Justin et al. | |
| 2009/0307887 A1 | 12/2009 | Jones et al. | |

FOREIGN PATENT DOCUMENTS

| | | |
|---|---|---|
| EP | 1435223 A1 | 7/2004 |
| EP | 1522284 A2 | 4/2005 |
| EP | 1522284 A3 | 6/2005 |
| EP | 1905396 A1 | 4/2008 |
| EP | 1522284 B1 | 12/2008 |
| EP | 2055273 A1 | 5/2009 |
| EP | 2057969 A2 | 5/2009 |
| EP | 2057969 A3 | 3/2010 |
| EP | 1435223 B1 | 8/2010 |
| EP | 2055273 B1 | 12/2010 |
| EP | 2057969 B1 | 5/2011 |
| FR | 2926212 A1 | 7/2009 |
| WO | WO 2007/098549 A1 | 9/2007 |

OTHER PUBLICATIONS

European SR From Corresponding EPO Pat App. 11175823.1-2310, Dated Nov. 25, 2011, (7 Pages).

Zimmer Metasul LDH Large Diameter Head Surgical Technique, Enhancing Stability and Increasing Range of Motion, Available At Least As Early As Sep. 28, 2006 (19 pages).

* cited by examiner

SPIRAL ASSEMBLY TOOL

TECHNICAL FIELD

The present invention relates generally to the field of orthopedics, and more particularly, to an implant for use in arthroplasty.

BACKGROUND

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

Many designs and methods for manufacturing implantable articles, such as bone prostheses, are known. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur, rotational positioning of the upper portion of the prosthesis is limited, thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm, reproducible, locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component which has an upwardly extending post which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Current attempts to provide a device to adjoin components of a modular joint prosthesis are fraught with several problems. For example, the device may not provide sufficient mechanical advantage to securely lock the components. Further, the ergonomics available to lock the components may not be optimal. There is thus a need to provide for an assembly tool capable of alleviating at least some of the aforementioned problems.

SUMMARY

According to one embodiment of the present invention, an assembly tool for assembly of a first component of a prosthesis to a second component of the prosthesis for use in joint arthroplasty is provided. The tool includes a first member operably associated with the first component. The first member defines a first member longitudinal axis thereof. A second member is operably associated with the second component, and the second member defines a second member longitudinal axis thereof. A washer system is also included and is coupled to the second member. A drive mechanism is coupled to washer system, such that as the drive mechanism is activated, the washer system rotates about the second member longitudinal axis and expands along the second member longitudinal axis, wherein such movement further causes the second member to move relative to the first member along the second member longitudinal axis.

According to another embodiment of the present invention, a method for assembling a first component of a prosthesis to a second component of the prosthesis for use in joint arthroplasty is provided. The method includes using an assembly tool having a first member and a second member. The second member defines a second member longitudinal axis. The assembly tool also includes a washer system coupled to the second member and a drive mechanism coupled to the washer system. The first component of the prosthesis is inserted onto the second component of the prosthesis. The second member of the assembly tool is secured onto the second component of the prosthesis. The drive mechanism is activated, causing the second member to move relative to the first member along the second member longitudinal axis.

According to yet another embodiment of the present invention, an assembly tool for assembly of a first component of a prosthesis to a second component of the prosthesis for use in joint arthroplasty is provided. The tool includes a first member operably associated with the first component. The first member defines a first member longitudinal axis thereof. A second member is operably associated with the second component. The second member defines a second member longitudinal axis thereof, and the second member includes a tensile rod. A drive mechanism is coupled to the second member, such that as the drive mechanism is activated and reaches a predetermined load, the tension member breaks.

BRIEF DESCRIPTION OF THE DRAWINGS

For a more complete understanding of the present invention and the advantages thereof, reference is now made to the following description taken in connection with the accompanying drawings.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
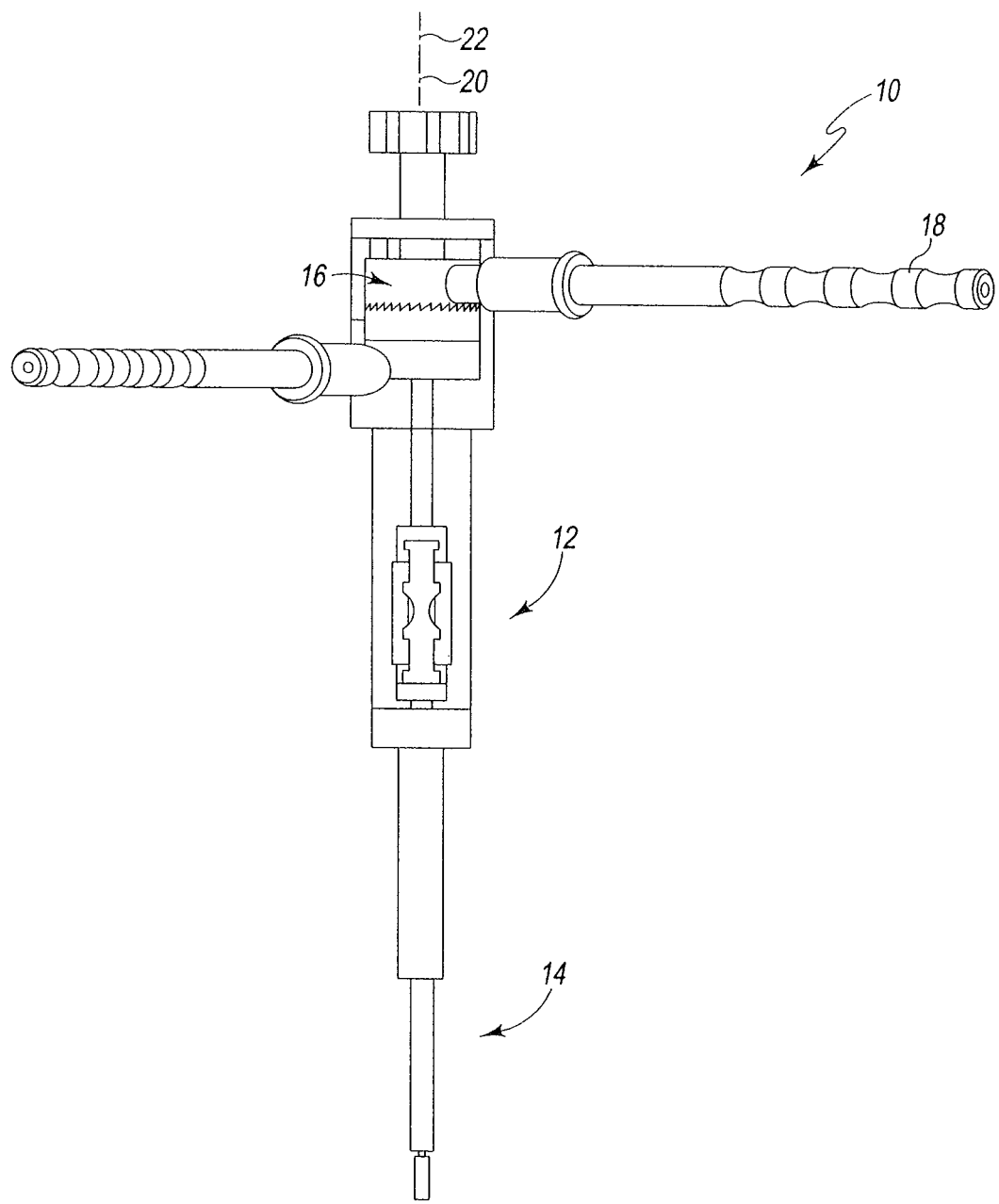
FIG. 1 is a see-through perspective view of an assembly tool according to one embodiment of the present invention.

FIG. 1 is a perspective view of an assembly tool 10 according to one embodiment of the present invention. The assembly tool 10 includes a first member 12 and a second member 14. Coupled to the second member 14 is a washer system 16. A drive mechanism 18 is coupled to the washer system 16. The first member 12 has a first member longitudinal axis 20 and the second member 14 has a second member longitudinal axis 22. In the illustrated embodiment, the first member longitudinal axis 20 and the second member longitudinal axis 22 are co-incident. In other embodiments, the two axes 20, 22 may be parallel or offset at an angle from one another. As the drive mechanism 18 is activated, it causes the washer system 16 to rotate about the second member longitudinal axis 22. In the illustrated embodiment, the drive mechanism is a handle that is ratcheted about the second member longitudinal axis 22. However, in other embodiments, it could be a longitudinal handle, a Hudson connection that connects to a power source, or other known drive mechanism that would cause the washer system 16 to rotate about the second member longitudinal axis 22.

Figure 2:
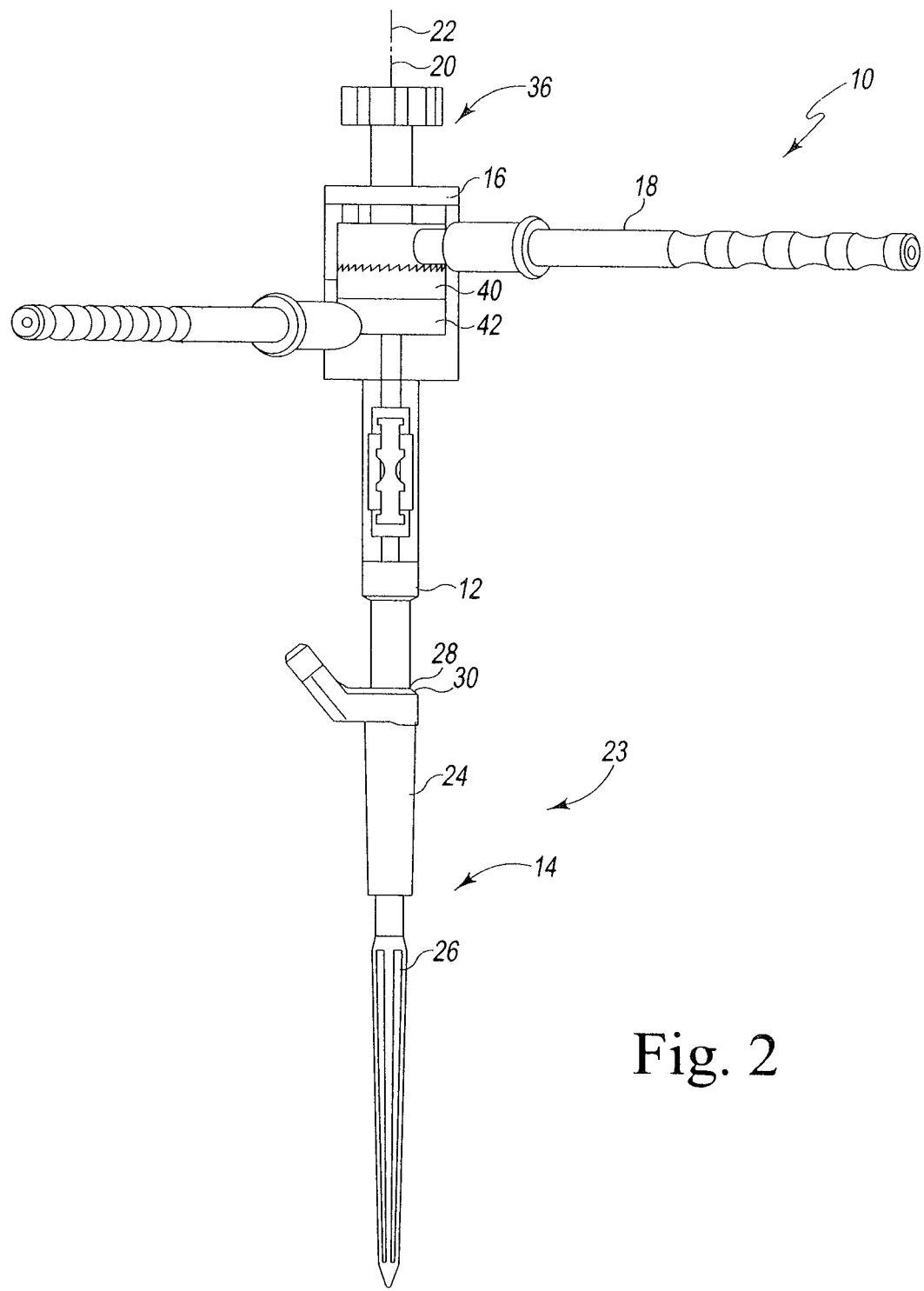
FIG. 2 is see-through view of the assembly tool of FIG. 1 coupled to a modular implant.

Referring now to FIG. 2, a see-through view of the assembly tool 10 is shown coupled to a modular implant 23. As shown, the modular implant 23 includes a first component 24 (or a proximal or neck component) and a second component 26 (or a distal or stem component). The first member 12 of the assembly tool 10 includes a distal end 28 that abuts a proximal end 30 of the neck component 24. In other embodiments, other connection means may be used. For example, the distal end 28 may include threads that engage a threaded end of the proximal end 30 of the neck component 24. Alternatively, the connection means may be a retractable button/recess system, a slotted l-shaped recess and rod system, an undercut, an expandable collet system, or any other known engagement system.

Figure 3:
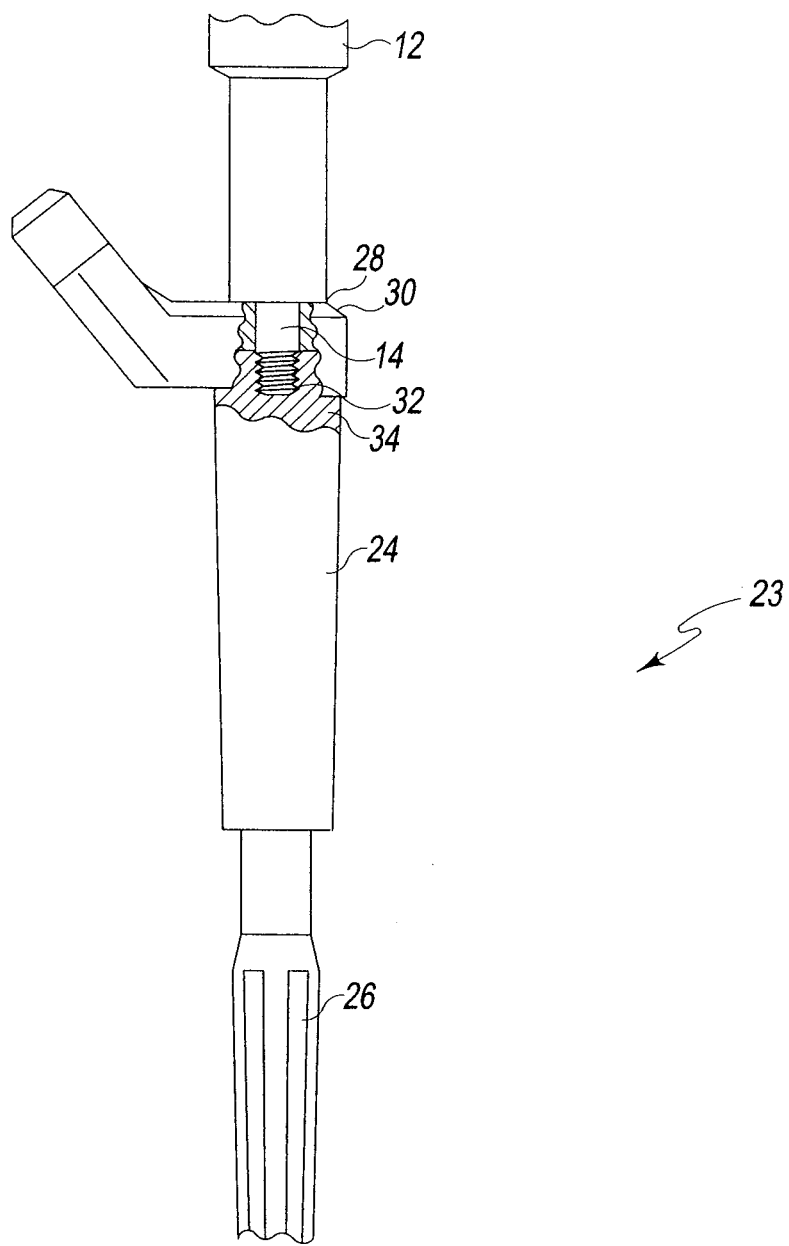
FIG. 3 is an enlarged see-through view of FIG. 2.

As shown in FIG. 3, a distal end 32 of the second member 14 engages a proximal end 34 of the stem component 26. In this embodiment, the distal end 32 of the second member 14 is threaded and fits inside a threaded bore of the proximal end 34 of the stem component 26. Alternatively, the distal end 32 of the second member 14 may have the threaded bore and the proximal end 34 of the stem component may be threaded. In other embodiments, other known means of connecting pieces may be used. For example, an expandable collet may be used. Alternatively, the connection means may be a retractable button/recess system, an undercut, a slotted l-shaped recess and rod system, an expandable collet system, or any other known engagement system.

Figure 4:
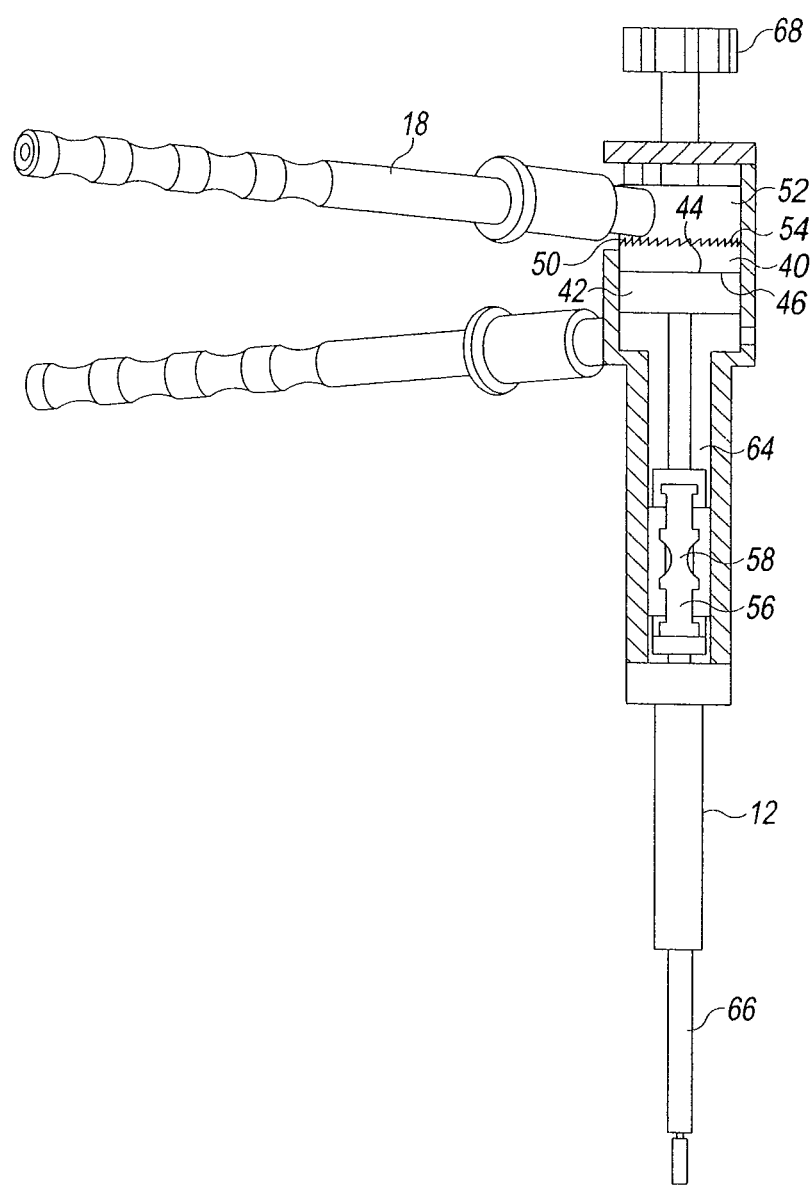
FIG. 4 is a perspective view of the assembly tool according to one embodiment of the present invention.

The second member 14 also includes a proximal end 36 (FIG. 2). The proximal end 36 includes a knob 68 (FIG. 4). The knob 68 is coupled to the threaded distal end 32, such that as the knob 68 is rotated about the second member longitudinal axis 22, the threaded distal end 32 is threaded into the threaded bore proximal end 34 of the stem component 26.

Figure 5:
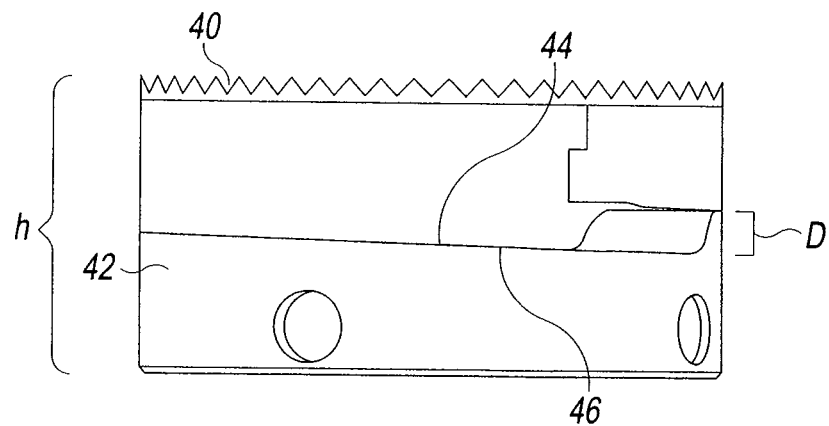
FIG. 5 is a perspective view of the washer assembly of FIG. 1.
Figure 6:
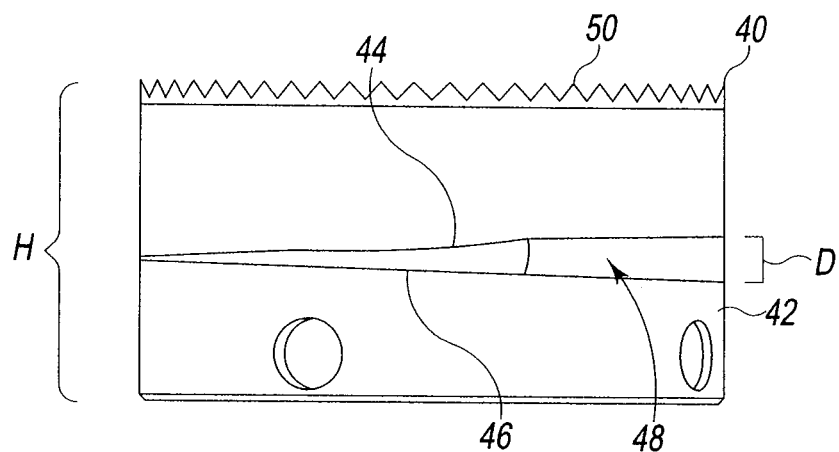
FIG. 6 is a perspective view of the washer assembly of FIG. 5 in a rotated position.

Turning now to FIGS. 4-6, the washer system 16 will be described. The washer system 16 includes a first spiral washer 40 and a second spiral washer 42. The first spiral washer 40 is coupled to the drive mechanism 18 and includes a first spiral ramp 44 and the second spiral washer 42 is coupled to the second member 14 and the first spiral washer 40 and includes a second spiral ramp 46 (FIG. 5). The first spiral ramp 44 abuts the second spiral ramp 46. The washer system 16 has an overall starting height of h. As the first spiral ramp 44 is rotated relative to the second spiral ramp 46, the ramps engage one another, creating a gap 48 between the first spiral washer 40 and the second spiral washer 42. The gap 48 is of a distance D. As shown in FIGS. 5 and 6, the washers 40, 42 begin by being flush against one another. However, as the first spiral washer 40 is rotated, the spiral ramps 44, 46 are rotated enlarging the height of the two washers 40, 42. The distance D of the gap 48 remains the same. In FIG. 6, the overall height of the washer system 16 is now H, which is larger than h. This change in height is generated by the opposing spiral ramps 44, 46 engaging one another, creating a washer system 16 with a variable height.

As shown in FIG. 4, the first washer 40 includes a ratchet end 50 that opposes the spiral ramp 44. The first washer 40 is coupled to a ratchet washer 52. The ratchet washer 52 is connected to the handle 18. One side 54 of the ratchet washer 52 is ratcheted and mates with the ratchet end 50 of the first washer. As the handle 18 is turned, the ratchets on the ratchet washer 52 and first spiral washer 40 engage one another, causing the first spiral washer 40 to rotate. Because the second spiral washer 42 is fixed, the two spiral ramps 44, 46 engage and cause the first spiral washer 40 to become raised (by a height D) relative to the second spiral washer 42.

Figure 7:
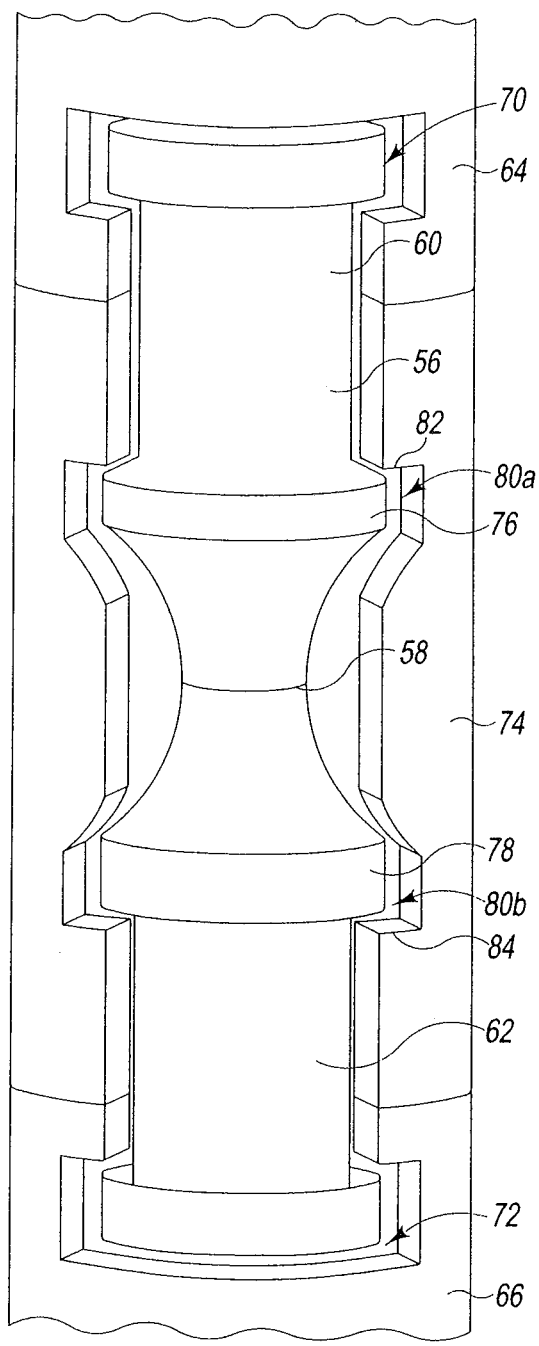
FIG. 7 is a cut-away view of a tensile rod assembly of the assembly tool of FIG. 1.

Referring still to FIG. 4 and also to FIG. 7, the second member 14 includes a sacrificial member 56, which in this case is a tensile rod or shear pin. The tensile rod 56 includes an intentional weak spot or breakage point 58. The breakage point 58 can only tolerate up to a specific tension. After that load (or tension) is reached, the breakage point 58 breaks, leaving two separate pieces 60, 62. As shown in FIG. 4, the tensile rod 56 links an upper part 64 of the second member 14 to a lower part 66 of the second member 14. As the handle 18 is turned, and the threaded distal end 32 of the second member 14 is threaded into the threaded bore of the proximal end 34 of the stem component 26, tension is created.

At the top of the upper part 64 of the second member 14, there is the knob 68, as described above. The knob 68 is turned to first thread the threaded end 32 of the second member 14 to the stem component 26.

Figure 7A:
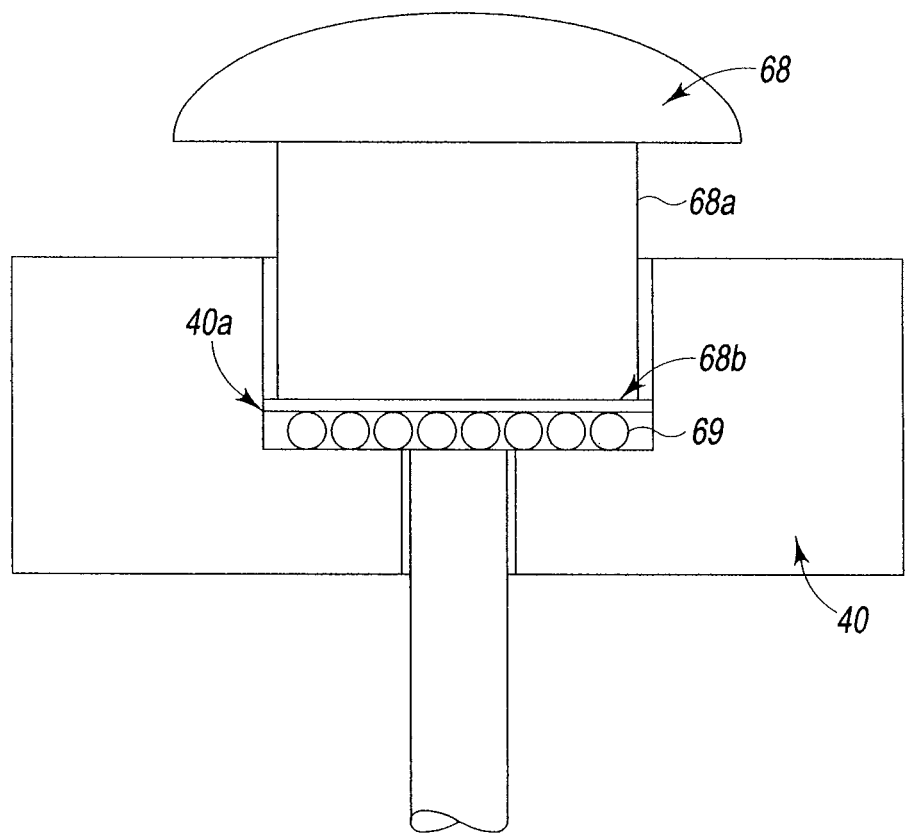
FIG. 7a is a close-up view of a washer system and a pull rod according to one embodiment of the present invention.

The knob 68 is coupled to the first spiral washer 40 in any number of known methods. In one embodiment illustrated in FIG. 7a, the knob 68 includes a pull rod 68a having a shoulder 68b. The shoulder 68b is coupled to a counterbore 40a in the first spiral washer 40, such that as the first spiral washer 40 rotates and moves upwards along the longitudinal axis 22, the knob 68 also moves upwards. In this embodiment, a bearing 69 is located between the shoulder 68b and the counterbore 40a. The bearing 69 illustrated is a rolling bearing and reduces the friction and torsional force felt by the pull rod 68a (and thus the sacrificial member 56). By reducing the frictional and torsional forces felt by the sacrificial member 56, the linear force at which the sacrificial member 56 will break is kept more consistent. In other embodiments, other types of bearings may be used. In some embodiments, no bearing 69 may be used and the shoulder 68b abuts the counterbore 40a directly.

As stated above, as the first spiral washer 40 rotates, and moves up along the longitudinal axis 22, the knob 68 also moves upwards. Because the knob 68 and threaded end 32 are coupled to one another and the threaded end is fixed within the stem component, the movement of the knob 68 creates tension along the second member 14. Once the tension reaches a certain force (or load), the tensile rod 56 will break at the breakage point 58. A loud noise will be heard; also the knob 68 will become loose. The tensile rod 56 breaking is important because it signals to the user that enough force has been applied. In this embodiment, the tensile rod 56 is fixed to break at a predetermined force. In some embodiments, that force is between about 2000 lbf and about 2500 lbf, and preferably at about 2250 lbf. In some embodiments, the knob 68 may also be used to disengage the ratchet washer 52 from the ratchet end 50 of the first washer 40.

As shown in FIG. 7, the two halves 60, 62 of the tensile rod 56 are each fitted into slotted openings 70, 72, respectively, of the second member 14. A sleeve 74 fits around the tensile rod 56. As shown, the first half 60 and the second half 62 each include a rib 76, 78 respectively, that extends outwardly. The ribs 76, 78 each fit within a recess 80a, 80b of the sleeve 74. The ribs 76, 78 also engage an edge 82, 84 of the recesses 80a, 80b. Once the tensile rod 56 breaks, both the first and second halves 60, 62 remain contained within the sleeve 74. Even though the first and second halves 60, 62 are no longer connected directly to one another, rotation of one will cause the other to rotate. As the knob 68 is rotated, the slotted opening 70 rotates. This rotation causes the first half 60 of the tensile rod 56 to rotate. When the first half 60 rotates, it engages the edge 82 of the sleeve 74, causing the sleeve 74 to rotate. As the sleeve 74 rotates, the edge 84 engages the second half 62, causing the second half 62 to rotate. The second half 62 rotating engages the slotted opening 72, causing the lower portion 66 of the second member 14 to rotate, disengaging the threaded end 32 from the stem component 26. In another embodiment, the two halves 60, 62 of the tensile rod 56 are keyed together, such that even after the halves 60, 62 break, they are still coupled together. Then, when one half rotates, the other half also is forced to rotate.

In the above embodiment, the tensile rod 56 is held by the second member. However, in other embodiments, it may be held by the first member. Also, any known containment method may be used. Alternatively, the tensile rod 56 need not be contained.

In some embodiments, the sacrificial member 56 may not be a tensile rod, but could be a torsional member. Once loads are applied on a longitudinal axis, the torsional member feels rotational force (e.g., a torsional spring). The torsional spring could be weakened so as to break at a certain force. In other embodiments, the sacrificial member 56 could be designed to fail in both axial and torsional directions.

Generally, the assembly tool 10 may be made from stainless steel. In some embodiments, the tensile rod 56 are made from 440C stainless steel, while all other components are made from 17-4 stainless steel. In other embodiments, the assembly tool 10 may be made of plastic, with only the washer system 16 and the tensile rod 56 being made of stainless steel. In other embodiments, other metals may be used. The tensile rod 56 could be made from plastic, ceramic, or other polymer. In other embodiments, the sleeve 74 could also be made of plastic or other polymer. In other embodiments, the assembly tool 10 may entirely be made of a single composite material. In some embodiments, the tensile rod 56 could be a small fixture with a shear pin.

In some embodiments, the distal end 28 of the first member 12 could include dimples that would create impressions on the proximal end of the neck component 24. The impressions would serve as a direct correlation to the force applied to the modular construct, much like those produced by a Rockwell hardness test machine. The spherical dimples on 28 could be positioned (clocked), such that, 3-impressions would be created in each use, regardless of the instrument-to-implant orientation. The physical size of the dimples would be predetermined, based on the material hardness of the proximal body. Other dimension (other than spherical) dimples could also be used. Alternatively, a number other than three dimples may be used.

In some embodiments, there may be a biasing mechanism, such as a wave spring or other type of spring, used to keep the ratchet washer 52 engaged with the ratchet end 50 of the first washer 40. Other springs may be used in the device to cause the first washer 40 to spring back after being ratcheted. In some embodiments, the spring may be a constant force spring.

Figure 8:
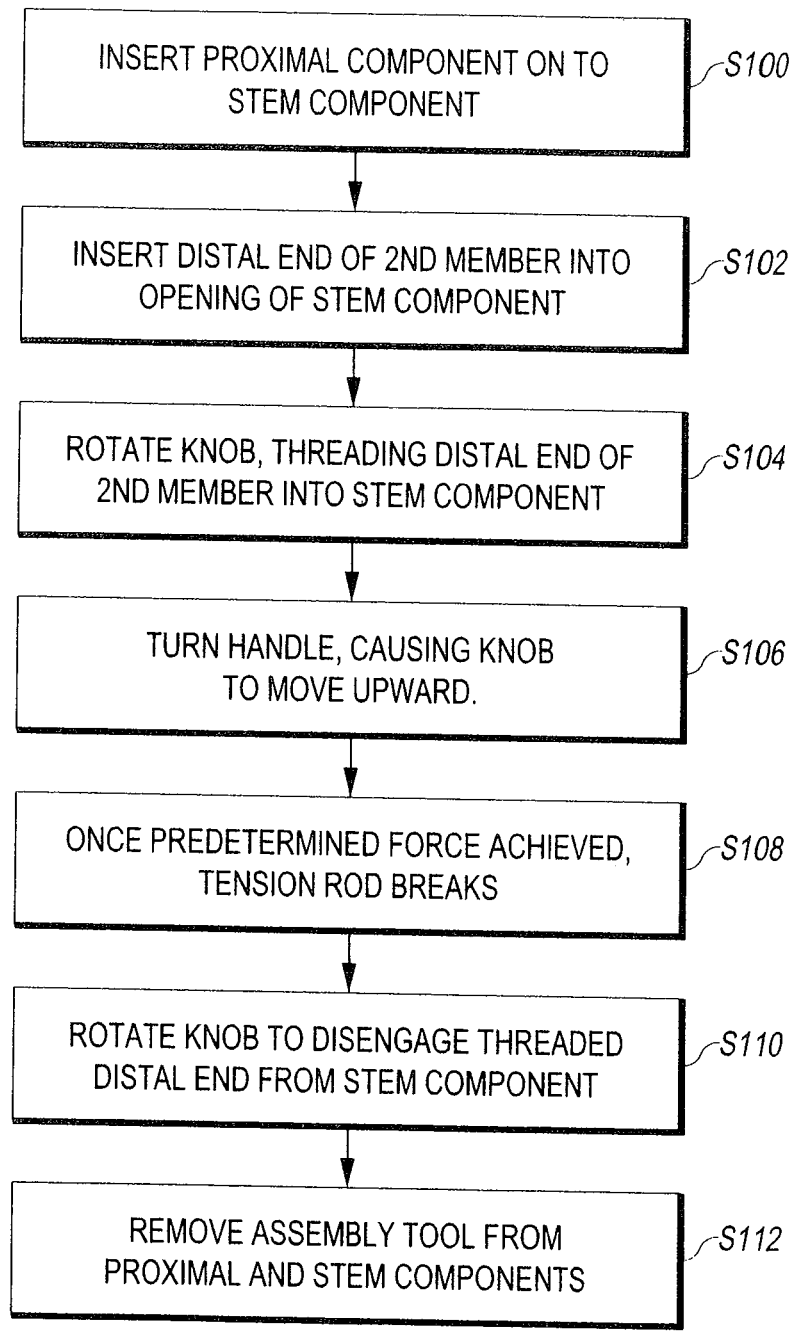
FIG. 8 is a flow chart of the method for using the assembly tool according to one embodiment of the present invention.

Turning now to FIG. 8, a flow chart describing the method of using the assembly tool 10 is shown. As shown, at step s100, the proximal component is inserted on to the stem component. Then the distal end of the second member is inserted into the opening of the stem component at step s102. When this is achieved, the distal end of the first member abuts the proximal end of the first component. At step s104, the knob is rotated threading the distal end of the second member into the stem component. The drive mechanism is then turned, causing the knob to move upward (step s106), as described above. Once a predetermined force is applied, the tensile rod breaks, indicating that the proper force has been applied (step s108). At step s110, the knob is rotated to disengage the threaded distal end from the stem component and the assembly tool is removed from the proximal and stem components (step s112).

Although the present invention and its advantages have been described in detail, it should be understood that various changes, substitutions, and alterations can be made therein without departing from the spirit and scope of the present invention as defined by the appended claims.

We claim:

1. An assembly tool for assembly of a first component of a prosthesis to a second component of the prosthesis for use in joint arthroplasty, the tool comprising:
   a first member operably associated with the first component, the first member defining a first member longitudinal axis thereof;
   a second member operably associated with the second component, the second member defining a second member longitudinal axis thereof;
   a washer system coupled to the second member, wherein the washer system includes a first spiral washer and a second spiral washer coupled to the second member and the first spiral washer; and
   a drive mechanism coupled to the washer system, the drive mechanism coupled to the first spiral washer, such that as the drive mechanism is activated, the washer system rotates about the second member longitudinal axis and expands along the second member longitudinal axis, wherein such movement further causes the second member to move relative to the first member along the second member longitudinal axis, the drive mechanism including a handle and wherein as the handle is rotated, the first spiral washer rotates relative to the second spiral washer and moves along the second member longitudinal axis relative to the second spiral washer;
   wherein the second member includes a tensile rod includes a portion that is thinner, such that the tensile rod breaks upon a certain amount of tensional force.

2. The assembly tool of claim 1, wherein the first spiral washer includes a first spiral ramp and the second spiral washer includes a second spiral ramp opposed the first spiral ramp, the first spiral ramp engaging the second spiral ramp such that as the first spiral washer rotates relative to the second spiral washer, the first and second spiral ramps engage, causing the first spiral washer to move along the second longitudinal axis relative to the second spiral washer.

3. The assembly tool of claim 1, wherein the drive mechanism is a handle and the first spiral washer has two sides, a spiral ramp side and a ratchet side, and the handle is connected to a washer having a ratchet, wherein the ratchet engages the ratchet side of the first spiral washer.

4. The assembly tool of claim 1, wherein the first member includes a component adapted to couple to the washer system and the tool further comprising a bearing between the component of the second member and the washer system.

5. The assembly tool of claim 1, wherein the tensile rod has a first part and a second part, the first and second parts being joined at a breakage point.

6. The assembly tool of claim 5, wherein the first and second parts are contained within a sleeve, such that after the tensile rod breaks, the first and second parts remain rotatably coupled via the sleeve.

7. A method for assembling a first component of a prosthesis to a second component of the prosthesis for use in joint arthroplasty, the method comprising:
   using an assembly tool having a first member and a second member, the second member defining a second member longitudinal axis, a washer system coupled to the second member and a drive mechanism coupled to the washer system, wherein the washer system includes a first spiral washer coupled to the drive mechanism and a second spiral washer coupled to the second member and to the first spiral washer, the second member further including a tensile rod having a portion that is thinner, such that the tensile rod breaks upon a certain amount of tensional force;
   inserting the first component of the prosthesis onto the second component of the prosthesis;
   securing the second member of the assembly tool onto the second component of the prosthesis;
   activating the drive mechanism, causing the second member to move relative to the first member along the second member longitudinal axis, wherein activating the drive mechanism includes rotating the first spiral washer relative to the second spiral washer and the first spiral washer moves along the second member longitudinal axis relative to the second spiral washer and wherein such activation of the drive mechanism results in locking the first component of the prosthesis to the second component of the prosthesis; and
   activating the drive mechanism to a predetermined force and the tensile rod breaking once the predetermined force is achieved.

8. The method of claim 7, wherein the second member includes a distal threaded end and securing the second member onto the second component comprises threading the distal threaded end of the second member into a threaded opening of the second component.

9. The method of claim 8, wherein the second member includes a knob and threading the distal threaded end comprises rotating the knob clockwise.

10. The method of claim 9, the method further comprising disengaging the distal threaded end from the threaded opening of the second component, the disengaging caused by rotating the knob counterclockwise.

11. The method of claim 7, wherein the first spiral washer includes a first spiral ramp and the second spiral washer includes a second spiral ramp, wherein rotating the handle causes the first spiral ramp to engage the second spiral ramp, causing the first spiral washer to move along the second longitudinal axis relative to the second spiral washer.

12. The method of claim 7, further comprising removing the assembly tool from the first and second stem components.

* * * * *

UNITED STATES PATENT AND TRADEMARK OFFICE
CERTIFICATE OF CORRECTION

| | | |
|---|---|---|
| PATENT NO. | : 8,533,921 B2 | Page 1 of 1 |
| APPLICATION NO. | : 12/815915 | |
| DATED | : September 17, 2013 | |
| INVENTOR(S) | : Steven R. Leisinger et al. | |

It is certified that error appears in the above-identified patent and that said Letters Patent is hereby corrected as shown below:

"Title page, Item (75) Inventors:, change 'Rodney N. Satterthwaite' to --Rodney E. Satterthwaite--."

Signed and Sealed this
Ninth Day of June, 2015

Michelle K. Lee
*Director of the United States Patent and Trademark Office*